United States Patent [19]

Taft

[11] 4,011,871

[45] Mar. 15, 1977

[54] WATER-DISPERSIBLE BARRIER FILMS FOR BODY FLUID RETENTION

[75] Inventor: Arnold Jay Taft, East Brunswick, N.J.

[73] Assignee: Personal Products Company, Milltown, N.J.

[22] Filed: Mar. 17, 1975

[21] Appl. No.: 559,205

[52] U.S. Cl. .............................. 128/284; 128/287; 128/290 R
[51] Int. Cl.² ........................................ C07C 87/30
[58] Field of Search ............. 260/77.5 AN, 77.5 Q, 260/29.2 TN; 428/290 R, 425; 128/284, 287, 290

[56] References Cited

UNITED STATES PATENTS

| | | | |
|---|---|---|---|
| 3,479,310 | 11/1969 | Dieterich et al. | 260/77.5 AM |
| 3,527,221 | 9/1970 | Croon et al. | 128/287 |
| 3,778,476 | 12/1973 | Rembaum et al. | 260/77.5 Q |
| 3,804,082 | 4/1974 | Tune | 128/284 |

*Primary Examiner*—George F. Lesmes
*Assistant Examiner*—R. J. Roche
*Attorney, Agent, or Firm*—Jason Lipow

[57] ABSTRACT

A barrier film is provided for a product used for retaining body fluids. The barrier film comprises a cationic polyurethane having an ionic charge density sufficient to render the film dispersible in aqueous solutions of relatively low ionic strength yet resistant to body fluids.

11 Claims, 6 Drawing Figures

U.S. Patent  Mar. 15, 1977  4,011,871
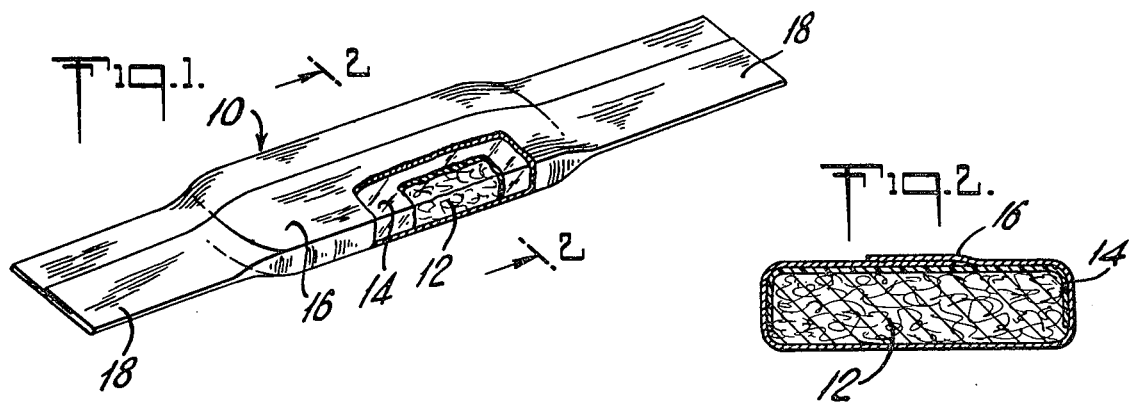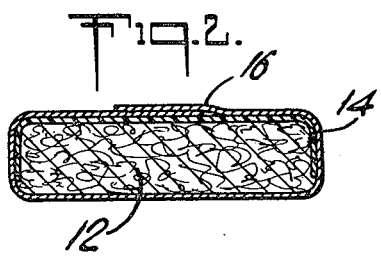
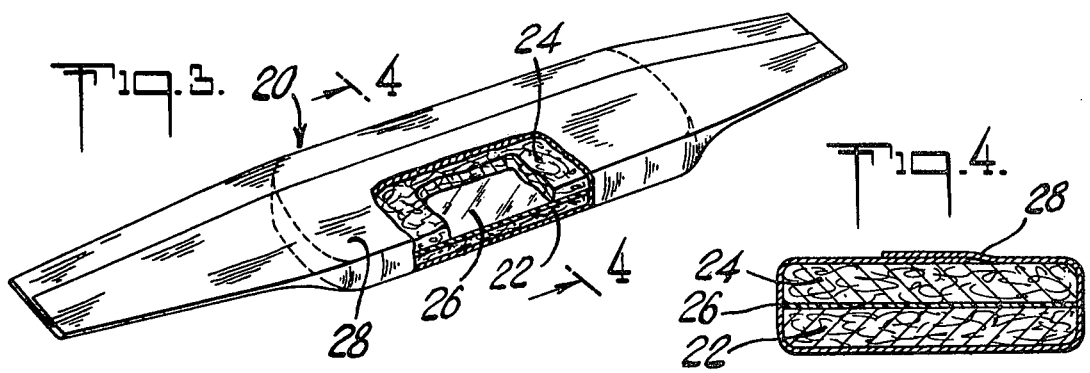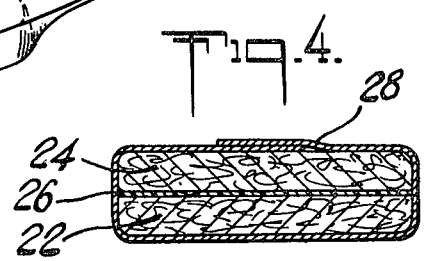
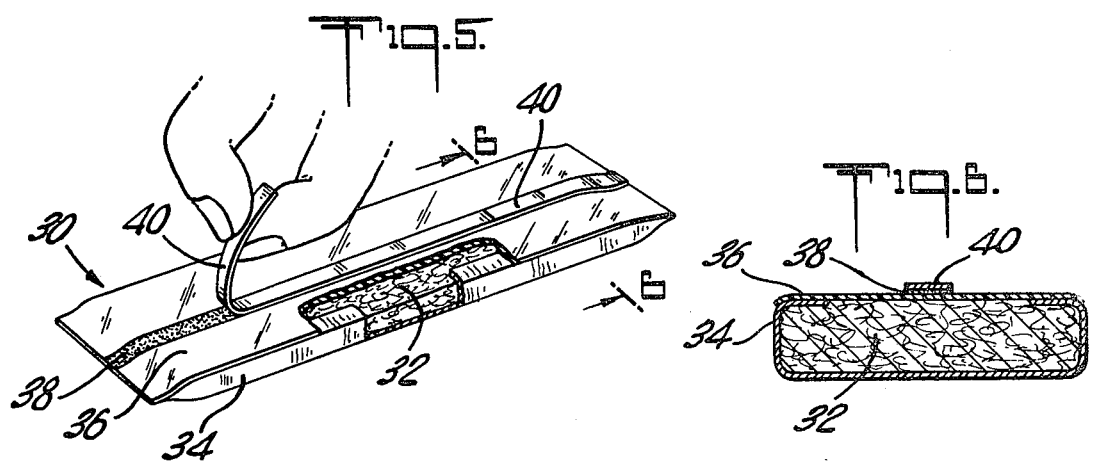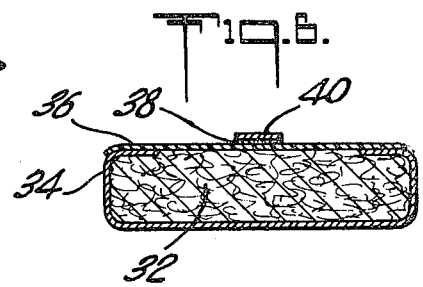

WATER-DISPERSIBLE BARRIER FILMS FOR BODY FLUID RETENTION

BACKGROUND OF THE INVENTION

This invention concerns the incorporation of protective barrier films in products used to retain fluids exuded from the body such as blood, menstrual fluid and urine. Specifically, the barrier films of this invention are useful in connection with absorbent products such as sanitary napkins, diapers, dressings and the like. The barrier films are likewise useful as liners for such products as bedpans and other receptacles. These films exhibit adequate tensile strength and retain their structural integrity when in contact with the aforesaid body fluids, yet are readily dispersible in water or aqueous solutions of relatively low ionic strength so that the film or the combination of film and product after use may be flushed away.

Heretofore, the choice of suitable barrier films has been extremely limited in that the desirable retention and dispersibility properties in films used for this purpose are infrequently found in combination. For example, the barrier film must be sufficiently strong to resist disintegration for a reasonable period of time when in use, i.e., the film must be insoluble or at least only slightly soluble in body fluids and must exhibit substantial tensile strength when subjected to such fluids. In addition, the barrier film must be readily dispersible in water so that the absorbent product can be conveniently flushed away. The choice of prior art barrier films adequately meeting these criteria has been extremely limited.

SUMMARY OF THE INVENTION

The present invention contemplates a product for retaining body fluids which includes a body fluid containing means and a barrier film dispersible in water and resistant to body fluids. The barrier film comprises a film of a cationic polyurethane having a repeating unit of the formula:

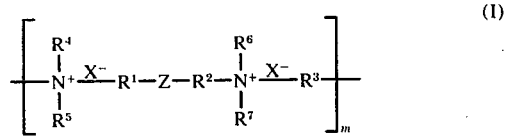

(I)

wherein $R^1$ and $R^2$ are selected from the group consisting of $-CH_2-$, and alkylene containing carbon atoms, inclusive, Z is a linking condensation residue of a polyisocyanate with a polyol and contains at least four urethane linkages, $R^3$ is alkenylene containing 2 to 4 carbon atoms, inclusive; $R^4$, $R^5$, $R^6$ and $R^7$ are lower alkyl groups containing 1 to 4 carbon atoms, inclusive; X is a halogen selected from the group consisting of chlorine and bromine; and $m$ is an integer of sufficient magnitude to provide a polymer having a molecular weight of sufficient magnitude to form a film; the equivalent weight of the polymer (based on ionic nitrogen) being no greater than about 2000. Preferably, $m$ has a value of about 10 to about 50. Preferably molecular weight of the cationic polyurethane is from about 8,000 to about 50,000.

It has now been discovered that these polymer films exhibit the unusual properties of retaining their tensile strength in salt solutions such as body fluids while readily dispersing in tap water.

The ionic polyurethanes used in the products of this invention are compatible with a wide range of readily available plasticizers which may be incorporated into the barrier film to produce a relatively noiseless, comfortable product such as an absorbent napkin or diaper without affecting its ability to disperse in water or its ability to retain body fluids.

BRIEF DESCRIPTION OF THE DRAWINGS

FIG. 1 is a perspective view of a sanitary napkin embodying this invention with parts broken away to show the interior construction thereof;

FIG. 2 is a cross-sectional view taken along plane 2—2 of FIG. 1;

FIG. 3 is a perspective view of a second sanitary napkin embodying this invention with parts broken away to show the interior construction thereof;

FIG. 4 is a cross-sectional view taken along plane 4—4 of FIG. 3;

FIG. 5 is a perspective view of an absorbent pad or undergarment liner embodying this invention with parts broken away to show the interior construction thereof; and FIG. 6 is a cross-sectional view taken along plane 6—6 of FIG. 5.

DETAILED DESCRIPTION OF THE INVENTION

The cationic polyurethane barrier films of this invention change the molecular configuration thereof in response to a change in the ionic strength of the medium to which these films are exposed. In a medium of relatively low ionic strength such as water, the ion-bearing polyurethane molecules generally assume a flexible linear, helical rod, or elliptical configuration, but the molecules change to a randomly convoluted configuration as the ionic strength of the medium increases. Barrier films prepared from ionic polyurethanes have maintained their structural integrity when immersed in aqueous 1 wt-% sodium chloride solutions, yet the same films have been found to readily disintegrate or become solubilized in tap water or distilled water. The barrier films can be prepared by condensing a polyisocyanate with a polyol and with a tertiary amino alcohol to produce a tertiary amine-capped condensation prepolymer which is then further reacted with a dihaloalkene to produce the polymeric material having the repeating unit shown in Formula I herein above.

The reaction between the polyisocyanate and the polyol is the well-known urethane-forming reaction which is preferably conducted in a solvent under anhydrous conditions and in the presence of a suitable catalyst such as stannous octoate, dibutyl tin dilaurate, or the like.

Polyisocyanates suitable for the purposes of the present invention can be aliphatic, aromatic, mixed aliphatic-aromatic, and can be of monomeric or polymeric length. Typical of such polyisocyanates are tolylene-2,4-diisocyanate (TDI), diphenylmethane-4,4'-diisocyanate (MDI), tolylene-2,3-diisocyanate, hexane-1,6-diisocyanate, naphthalene-1,5-diisocyanate, diphenyl-3,3'-dimethyl-4,4'-diisocyanate, diphenyl-3,3'-dimethoxy-4,4'-diisocyanate dietyl ether, 3-(diethylamino)pentane-1,5-diisocyanate, butane-1,4-diisocyanate, cyclohex-4-ene-1,2-diisocyanate, benzene-1,3,4-triisocyanate, naphthalene-1,3,5,7-tetraisocyanate, naphthalene-1,3,7-triisocyanate, toluidine diisocyanate, isocyanate-terminated prepolymers, polyarylpolyisocyanates, and the like. Illustrative of the commercially-available polyarlypolyisocyanates is a polymethylene polyphenyl polyisocyanate known under the designation PAPI-1 and available from the Upjohn Company. This particular polyisocyanate has an average molecular weight of about 380 and an average of about 3 isocyanate groups per molecule. Another suitable polyisocyanate is a poly(1,4-oxybutylene)-based diisocyanate terminated prepolymer known under the designation ADIPRENE L-100 (molecular weight about 2050) and ADIPRENE L-167 (molecular weight about 1330), both available from the E. I. duPont de Nemours & Co. of Delaware. Still other commercially available higher molecular weight polyisocyanates are a polyester terminated with isocyanate groups known under the designation MULTRA-THANE-242 F available from the Mobay Chemical Corporation of Pittsburgh, Pennsylvania and a triisocyanate derivative of glycerol and ricinoleic acid known under the designation SOLITHANE 113 available from the Thiokol Chemical Corporation of Delaware.

Suitable polyols for the present purposes are the polyether polyols such as polyethylene glycol, polypropylene glycol, polybutylene glycol and the like, which have ether linkages or the polyester polyols such as polycaprolactone and the like, which have ester linkages and polyester-polyether block copolymers thereof which have both ether linkages and ester linkages. For biodegradability, particularly preferred are the aliphatic polyester polyols such as polycaprolactone having a molecular weight in the range of about 800 to about 2000, alone or in combination with a polyether polyol.

Illustrative of the tertiary amino alcohols are 1,3-bis(dimethylamino)-2-propanol, 2-dimethylaminoethanol, p-dimethylaminophenol, and the like.

In preparing the tertiary amine-capped prepolymers, the foregoing reactants can be added sequentially or in a single step, as desired. Suitable solvents for carrying out the reaction are methylethylketone, dimethylformamide, tetrahydrofuran, and the like.

Thereafter, the prepared tertiary-amine prepolymer is alkylated, i.e., quaternized by adding a dihaloalkene such as trans-1,4-dichloro-2-butene (TDCB), trans 1,4-dibromo-2-butene-3,4dichloro-1-butene, or the like, to the reaction mixture at a temperature of about 20° C. to about 100° C., and preferably at a temperature of about 50° C. to about 60° C. An unsaturated alkylating agent may be used in order to increase reactivity. The resulting ionic polyurethane polymer can then be cast into films of desired thickness.

The overall reaction sequence can be illustrated as follows:

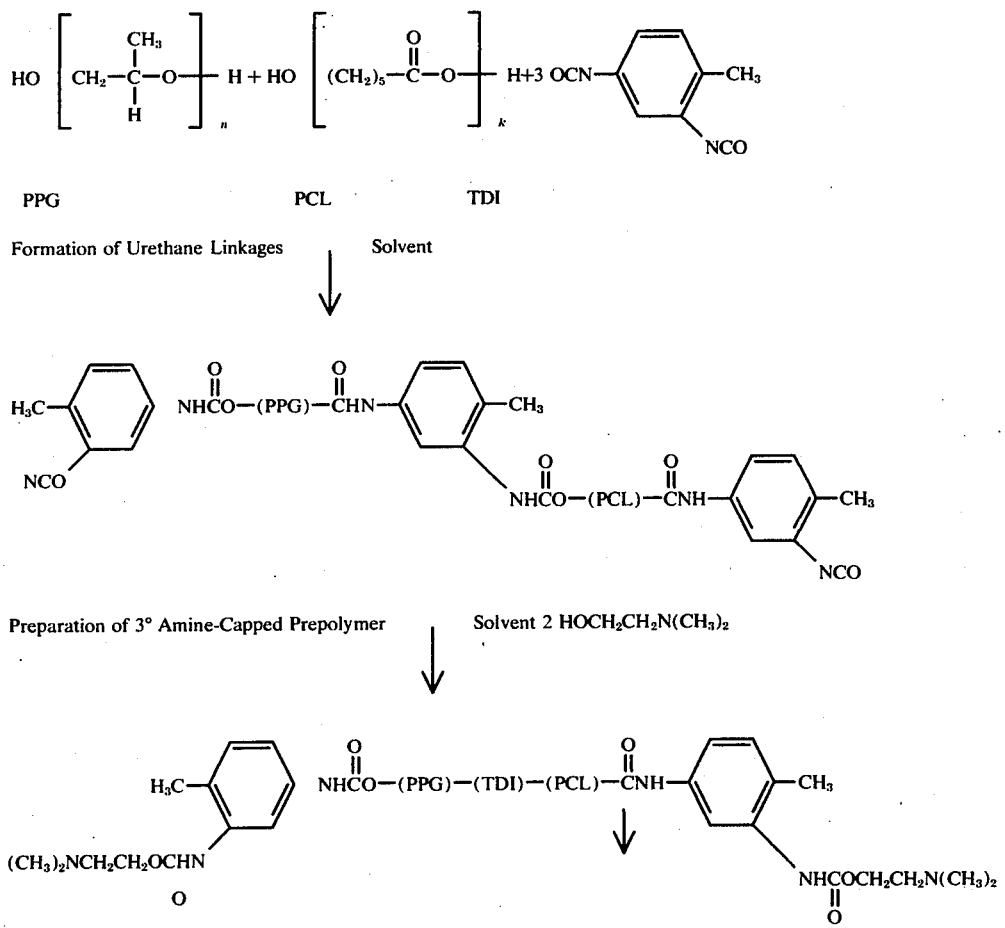

-continued

Quaternizing Polyaddition                                                                    $ClCH_2CH=CHCH_2Cl$

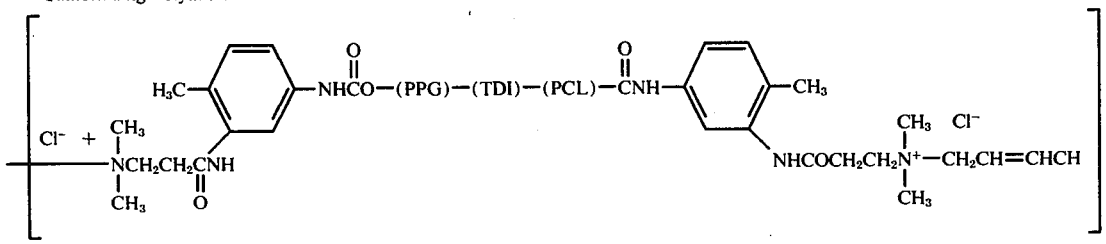

Films of the ionic polyurethane polymers may be cast by dissolving the polymer in a suitable solvent, applying the solution onto a release surface and allowing the solvent to evaporate, leaving behind a film which is then peeled from the release surface. A wide variety of solvents may be used including, for example, water, methanol, ethanol, methylethyl ketone, dimethylformamide, tetrahydrofuran, nitrobenzene, dimethylsulfoxide or various combinations of these. The resin concentrations are limited, on the one hand, by the necessity for maintaining the solution sufficiently dilute so as to exhibit good fluidity and, on the other hand, by the necessity for maintaining the solution sufficiently concentrated so as to limit the volume to be handled to a convenient quantity. In general, it has been discovered that films having thicknesses varying from 0.1 to 5.0 mils can conveniently be prepared from solutions containing about one to about ten percent by weight of ionic polyurethane and preferably from solutions containing about two to five percent by weight of the polymer. The films are cast on suitable release surfaces such as silicon or fluorocarbon resin- (Teflon) coated surfaces. For example, excellent translucent, peelable films are obtained from an ionic polyurethane resin dissolved in a 3 to 4% w/w methanol solution and cast, at room temperature, onto a Teflon-coated pan.

The films of this invention, cast from ionic polyurethane resins, are uniquely suited for use as flushable barrier films in a product used in contact with such body fluids as blood, menstrual fluid, urine, etc. These fluids, in general, exhibit properties which, with respect to the films, are analogous to an aqueous salt solution having a salt content which varies from about 0.8 to about 1.5 percent by weight of sodium chloride. On the other hand, the tap water normally supplied to water closets and the like generally has an extremely low salt concentration of less than about 250 parts per million of chloride ion. It has been discovered that the barrier films of this invention maintain their integrity for a substantial period of time in solutions having a salt concentration exhibiting the properties of body fluids, whereas, surprisingly, these films display a far lower resistance to dispersion in tap water. In addition, by modifying the ionic charge density of these polymers, the salt resistance and water dispersibility of the films can be modified to suit the particular purposes of this invention, i.e., to form films which will adequately provide a barrier for body fluids for a suitable length of time yet which may be flushed away.

Specifically, by lowering the ionic charge density, the barrier films of this invention become more resistant to dispersion in water. However, if the ionic charge density is increased, the films maintain structural integrity in body fluids yet remain water-dispersible. On the other hand, if the ionic charge density is too high, the films lose structural integrity in body fluids. The ionic charge density for the ionic polyurethane resin is an inverse function of the equivalent weight of the polymer expressed as the ratio of the molecular weight of the repeating unit in the polymer chain divided by the number of $N^+$ in the repeating unit, i.e., as the equivalent weight increases, the ionic charge density decreases and vice versa. In general, an equivalent weight of about 500 to about 2000 is desirable for the present barrier films when used in connection with body fluids. Preferably, the equivalent weight should be in the range of about 750 to about 1400. While the resistance of the barrier films to salt solutions having a salt concentration exhibiting the properties of body fluids increases with decreasing charge density, the ability to disperse readily in tap water is maintained until relatively low charge density values are reached. Adequate tap water-dispersibility is achieved, however, when the equivalent weight is maintained at a value not greater than about 2000.

The barrier films of this invention are highly compatible with a great variety of plasticizers, thus such plasticizers may be incorporated therein to improve such film characteristics as flexibility, resistance to abrasion, and "noise", i.e. the rattle resulting from the flexing of the film. These properties are particularly important when the barrier films are used in connection with items to be worn such as the aforementioned sanitary napkins, diapers and the like. For these purposes, water-soluble plasticizers such as glycerol and polyethylene glycol can be used, as well as water-insoluble plasticizers such as castor oil, and the like.

When the films of this invention are used in connection with such products as liners for bedpans and other receptacles for body fluids comprising a relatively rigid vessel adapted to receive an inner liner, they may be cast directly on the inside surface of the receptacle prior to use or may alternatively be precast and then applied to the receptacles. After fluid has been received into the lined receptacle, the entire liner together with the retained fluid may be lifted out of the receptacle and disposed of in a water closet. The films of this invention exhibit sufficient tensile strength when in contact with the body fluid to allow the liner to be lifted out of the receptacle, yet at the same time are completely dispersible in tap water so as to be readily flushable.

Referring now to the drawings, FIGS. 1 and 2 illustrate an embodiment of the films of this invention as used in sanitary napkin 10 which comprises absorbent core 12 of fibrous material such as comminuted wood pulp fibers, cotton linters, rayon fibers, cotton staple, bleached sulfite linters, other cellulosic or modified cellulosic fibers and the like. Overlying the bottom surface of the absorbent core (that portion of the napkin worn away from the body) is a thin barrier sheet 14 made of an ionic polyurethane film. Fluid pervious cover 16 surrounds absorbent core 12 and barrier sheet 14, with the lateral edges thereof overlapped and secured to the bottom surface of napkin 10. Cover 16 can be extended beyond the ends of core 12 to form the usual attachment tabs 18. While FIGS. 1 and 2 illustrate a tabbed napkin, it will be understood by one skilled in the art that the advantages according to the use of barrier films of this invention are equally applicable to a tabless product, e.g., one where tabs are not used as attachment means and other attachment means such as, for example, adhesive means, are used, as well as to a disposable diaper comprising an absorbent pad and a backing sheet therefor made from the barrier film.

As incorporated into the product shown in FIGS. 1 and 2, the water-dispersible barrier sheet, comprising films of this invention, is uniquely suited to preclude the passage of menstrual fluid or the like through the core to the bottom surface of the napkin. Menstrual fluid, as other body fluids, exhibits properties, with respect to the film, which are analogous to the aqueous solution having a salt content of about 0.8 to about 1.5 percent by weight and it is within these concentrations that the films of this invention are resistant and impermeable. Notwithstanding the resistance of the films to menstrual fluid, when the films are introduced into an aqueous low salt concentration solution, they are water-dispersible. Accordingly, by employing a water-dispersible material for cover 16 (as well as a water-dispersible core 12) the sanitary napkins of FIGS. 1 and 2 can be completely disposed of in a water closet. Alternatively, the illustrated napkin may be provided with a non-water-dispersible cover, in which event the cover would first be removed and the pad and barrier film dropped into a water closet for disposal. In either event, the unique barrier film of this invention will completely disperse in a water closet under the swirling action of the low salt concentrations found therein, and will not clog or otherwise impair the operation of the water closet and associated plumbing.

FIGS. 3 and 4 illustrate a second embodiment of this invention in a napkin of alternative construction. Sanitary napkin 20 is provided with first and second absorbent layers 22 and 24. Sandwiched therebetween is barrier sheet 26 comprising an ionic polyurethane film of this invention. Fluid pervious cover 28 surrounds absorbent layers 22 and 24, the lateral edges thereof being overlapped and secured on the bottom surface of napkin 20. As in the embodiment of FIGS. 1 and 2, the cover is illustrated as extending beyond the absorbent layers to form attachment tabs, although it is equally advantageous to use the teachings of this invention in a tabless product. Again the present films are uniquely suited for use as barrier films which preclude the passage of menstrual fluid to the bottom of the napkin but which are completely dispersible in water. Hence, if napkin 20 is provided with a water-dispersible cover, it may be completely disposed of by flushing or, alternatively, if the napkin is provided with a water-resistant cover, such as a polyethylene film, or the like, the cover may be first removed and the remainder of the napkin then can be disposed of by flushing. A particular advantage of a napkin having the construction illustrated in FIGS. 3 and 4 is that the barrier film located between absorbent layers is less likely to exhibit "noise" which could embarrass the wearer, and hence the need for the addition of plasticizers to the film is lessened.

In this connection, it will be apparent to one skilled in the art that, while two separate absorbent layers have been illustrated, many alternatives are possible, such as, for example, the use of multiple layers or the forming of the layers by simply folding a single sheet of absorbent material.

FIGS. 5 and 6 illustrate still another embodiment of this invention. Illustrated therein is absorbent pad 30 which is useful as a protective cover for undergarments. Pad 30 is provided with absorbent core 32 and fluid pervious cover 34 overlies the top (the surface worn against the body) and side portions thereof, the lateral edges also overlying the peripheral portions of the bottom surface of core 32. Barrier film 36 is provided to overlie the bottom surface of the core and those portions of cover 34 which overlie the bottom surface. Barrier sheet 36 and cover 34 are secured together and preferably are also anchored to core 32. The outer surface of the barrier sheet is provided with adhesive means 38 which can be, for example, a layer of pressure-sensitive adhesive or a double-faced adhesive tape. Adhesive means 38 is protected, prior to use, by strippable, peelable cover 40. In use, cover 40 is stripped from the napkin exposing adhesive means 38. The napkin is then placed, for example, in the crotch portion of a panty or similar undergarment and held in place by adhereing the barrier film portion to the panty. Once again, the unique features of the barrier film allow the pad to be readily disposed of by flushing.

It will be appreciated by one skilled in the art that the present barrier films can be designed to particularly function in a specific capacity. For example, when used in sanitary napkins, it is clear that the barrier films contact only absorbent materials dampened with menstrual fluid, whereas when the napkins are disposed of, the napkins are fully immersed in swirling tap water. Accordingly, barrier films used for those purposes may be designed so as to be thinner and a relatively wider range of polymer ionic charge densities may be employed. On the other hand, where the barrier films are used as a liner for bedpans, the films are in more substantial contact with the body fluid and may have to remain in such contact for a considerable time period. Accordingly, thicker, more saline resistant films, i.e., films having a relatively lower and narrower range of polymer ionic charge densities, should be used.

In forming the barrier films, the ionic polyurethanes can be combined also with filler materials. When cast into film form such filler modified films will continue to exhibit the desired features of saline resistivity and water-dispersibility. Suitable filler materials are titanium dioxide, kaolin and acrylic resin.

The invention will be more readily understood by consideration of the following examples which describe specific embodiments exemplifying the invention and the methods of making and using the same.

EXAMPLE 1

A series of ionic polyurethane polymers are prepared using as the starting material a prepolymer obtained from the duPont Company and sold by them under the trademark ADIPRENE. This prepolymer consists of a diisocyanate terminated poly(1,4-oxybutylene) and has a number average molecular weight of about 1330. The prepolymer is combined with 2-dimethylaminoethanol in a benzene solution and allowed to react therewith at a temperature of 60°–70° C for about 1.5 hours. A quantity of trans-1,4,-dichloro-2-butene is then added to the reaction mixture which is then allowed to further react at the above given temperature for seven additional minutes. A quantity of 4,4'-methylene-bis-(2-chloroaniline) is then added to the system and the reaction mixture is then cured for about 18 hours at a temperature of about 50°–60° C. with stirring. The proportions of the components used and the resulting polymer equivalent weight (the molecular weight of the repeating unit divided by the number of $N^+$ in the repeating unit) are given in Table I below.

quaternized by lowering the reaction mixture temperature to about 50°–60° C. and adding a quantity of trans-1,4,-dichloro-2-butene.

The reaction mixture is cured by maintaining the mixture at about 50° C to 60° C while stirring. The proportions of the various components, the curing times and the equivalent weight of the resulting ionic polyurethane polymers are given in Table II.

TABLE II

| | Mole Ratio of Components | | | | | | |
|---|---|---|---|---|---|---|---|
| SAMPLE | POLY-CAPROLACTONE POLYOL | POLY-PROPYLENE GLYCOL | DIMETHYLAMINO ETHANOL | TOLYLENE DIISOCYANATE | DICHLORO BUTENE | CURING TIME (HRS) | EQUIVALENT WEIGHT |
| 3 | 0.25 | 0.75 | 4.0 | 3.0 | 2.1 | 18 | 780 |
| 4 | 0.25 | 0.75 | 2.0 | 2.1 | 1.0 | 18 | 1330 |
| 5 | 0.25 | 0.75 | 2.0 | 2.6 | 1.0 | 18 | 1380 |
| 6 | 0.25 | 0.75 | 2.0 | 2.6 | 1.2 | 18 | 1392 |
| 7 | 0.25 | 0.75 | 2.0 | 2.0 | 1.0 | 18 | 1320 |
| 8 | 0.25 | 0.75 | 4.0 | 3.0 | 2.1 | 18 | 780 |
| 9 | 0.25 | 0.75 | 2.0 | 2.1 | 1.0 | 18 | 1330 |
| 10 | 0.25 | 0.75 | 2.0 | 2.6 | 1.0 | 18 | 1380 |
| 11 | 0.25 | 0.75 | 4.0 | 3.0 | 2.0 | 24 | 790 |
| 12 | 0.25 | 0.75 | 4.0 | 3.0 | 2.0 | 144 | 790 |
| 13 | 0.25 | 0.75 | 2.0 | 2.6 | 1.2 | 24 | 1380 |
| 14 | 0.25 | '' | '' | '' | '' | 240 | 1380 |
| 15 | 0.25 | 0.75 | 2.0 | 2.2 | 1.0 | 24 | 1340 |
| 16 | 0.25 | '' | '' | '' | '' | 168 | 1340 |
| 17 | 0.25 | 0.75 | 2.0 | 2.2 | 1.0 | 24 | 1340 |
| 18 | 0.25 | '' | '' | '' | '' | 120 | 1340 |
| 19 | 0.25 | 0.75 | 4.0 | 3.0 | 2.0 | 24 | 790 |
| 20 | 0.25 | '' | '' | '' | '' | 216 | 790 |
| 22 | 0.25 | 0.75 | 2.0 | 2.1 | 1.0 | 24 | 1320 |
| 23 | 0.25 | '' | '' | '' | '' | 72 | 1320 |
| 24 | 0.25 | '' | '' | '' | '' | 24 | 1320 |
| 25 | 0.25 | '' | '' | '' | '' | 168 | 1320 |

TABLE I

| | | Molar Ratio of Components | | | |
|---|---|---|---|---|---|
| Sample | Prepolymer | 2-Dimethylamino ethanol | Dichlorobutene | Methylene Chloroaniline | Equiv. Weight |
| 1 | 1 | 1.8 | 0.9 | 0.1 | 920 |
| 2 | 1 | 1.7 | 0.85 | 0.15 | 970 |

EXAMPLE 2

A second series of ionic polyurethanes, as prescribed herein, are prepared by combining, in methylethylketone, a quantity of polycaprolactone polyol having a number average molecular weight of about 2000 with polypropylene glycol having a number average molecular weight of about 2025 and 2-dimethylaminoethanol. A quantity of 2.4 tolylene diisocyanate and stannous octoate (as catalyst) is added and the mixture is permitted to react at about 60° to 70° C for 6 hours. The resulting tertiary amine-capped prepolymer is then

EXAMPLE 3

A third series of ionic polyurethanes, as prescribed herein, are prepared by combining a quantity of polypropylene glycol having a number average molecular weight of about 2025 with 2-dimethylaminoethanol. A quantity of 2,4-tolylene diisocyanate and stannous octoate (as catalyst) is added and the mixture is permitted to react at 60°–70° C for 6 hours. The resulting tertiary amine-capped prepolymers is then quaternized by adding a quantity of trans-1,4-dichloro-2-butene to the reaction mixture which is lowered to a temperature of about 50°–60° C and then cured for a specified period of time with mixing. The properties of the components, the curing times and the equivalent weight of the resulting ionic polyurethanes obtained are given in Table III.

TABLE III

| | Mole Ratio of Components | | | | | |
|---|---|---|---|---|---|---|
| SAMPLE | POLYPROPYLENE GLYCOL | DIMETHYLAMINO ETHANOL | TOLYLENE DIISOCYANATE | DICHLORO BUTENE | CURE TIME (HOURS) | EQUIVALENT WEIGHT |
| 26 | 1 | 2.0 | 2.1 | 1.0 | 1 | 1340 |
| 27 | '' | '' | '' | '' | 7 | 1340 |
| 28 | 1 | 2.0 | 2.0 | 1.0 | 1 | 1320 |
| 29 | '' | '' | '' | '' | 24 | 1320 |
| 30 | '' | '' | '' | '' | 1 | 1320 |

TABLE III-continued

| | Mole Ratio of Components | | | | | |
|---|---|---|---|---|---|---|
| SAMPLE | POLYPROPYLENE GLYCOL | DIMETHYLAMINO ETHANOL | TOLYLENE DIISOCYANATE | DICHLORO BUTENE | CURE TIME (HOURS) | EQUIVALENT WEIGHT |
| 31 | " | " | " | " | 24 | 1320 |

EXAMPLE 4

Films are prepared from the ionic polyurethanes of the foregoing examples to illustrate the dry strength properties of these films as well as the difference in wet properties when comparing their behavior in various liquid media.

In each case, the ionic polyurethane films are prepared by dissolving the ionic resin in methanol so as to form about 3–5% by weight methanol solutions. The above concentration gave good fluidity (a viscosity of about 15 cps at 25° C) and at these concentrations, films may be prepared having a thickness of from 0.5 to 3 mil while using reasonable volumes of solution. The films are cast in 8 × 8 inch Teflon-coated or silicone-coated pans. The data reported in Table IV below is based on film samples prepared as described above, each sample measuring 10 mm by 10 mm and being 2 mils thick. Reduced viscosity measurements as reported below are made by the method described in *Text Book of Polymer Science*, W. Billmayer, Interscience (1965). The solvent used in all cases for reduced viscosity measurements is dimethyl sulfoxide and for samples 3 through 10, the solution of polymer is at a concentration of 0.25% by weight, whereas for samples 11 through 31, the concentration is 2.0% by weight. Dry tensile and Ultimate Elongation data are obtained using an Instron Tensile Tester with the jaw space set at a distance of two inches and the crosshead speed maintained at two inches per minute.

The samples are tested to contrast the wet properties they exhibit in distilled water, in a 1% by weight sodium chloride solution and, for the two cases noted in Table IV, in pooled samples of menstrual fluid. The samples are immersed in each liquid media for the time specified below and the condition of the film at the end of this time period is noted either qualitatively or quantitatively. Qualitatively, the condition is described as Dissolved; Considerable Loss of Integrity (Consid. LOI, where the film has broken up into large fragments); or Complete Loss of Integrity (Comp. LOI, where the film has broken up into small fragments).

Where the wet properties are quantitatively expressed in Table IV, this data refers to the percent elongation in the original length of the film (EOL) as a result of immersion; the greater the percent elongation, the weaker the film. It should be noted that where percent elongation is recordable, (i.e., where quantitative values are given), the film is stronger than those samples for which wet properties are reported qualitatively.

TABLE IV

| | | | DRY PROPERTIES | | | WET PROPERTIES (EOL in %) | | |
|---|---|---|---|---|---|---|---|---|
| | | | | | | | SOLUTION | |
| SAMPLE | CURE TIME (HRS.) | EQUIV. WT. | REDUCED VISCOSITY (CENTIPOISES) | TENSILE STRENGTH (PSI) | ULTIMATE ELONGATION (%) | IMMERSION TIME (MIN.) | DISTILL. H₂O | 1% SALINE H₂O | MENSTRUAL FLUID |
| 1 | 18 | 920 | — | — | — | 20 | Dissolved | 20 | — |
| 2 | 18 | 970 | — | — | — | 20 | 70% | 10 | — |
| 3 | 18 | 780 | 1.18 | 120 | 510 | 20 | Dissolved | 60 | 20 |
| 4 | 18 | 1330 | 0.35 | 60 | 210 | 20 | Comp. LOI | 10 | — |
| 5 | 18 | 1380 | 0.86 | 120 | 920 | 20 | Consid. LOI | 15 | 5 |
| 6 | 18 | 1390 | 0.77 | 100 | 1020 | 20 | Comp. LOI | 15 | — |
| 10 | 18 | 1380 | 0.37 | 60 | 480 | 20 | — | — | — |
| 11 | 24 | 790 | 0.46 | 120 | 420 | 1/60 | Cons/Dissol. | 15/50 | — |
| 12 | 144 | 790 | 0.55 | 160 | 880 | 1/60 | 70/Dissol. | 15/70 | — |
| 13 | 24 | 1380 | 0.37 | 100 | 540 | 1/60 | 50/Consid. | 5/10 | — |
| 14 | 240 | 1380 | 0.93 | 200 | 1200 | 1/60 | 60/Comp. | 5/20 | — |
| 15 | 24 | 1340 | 0.36 | 80 | 370 | 1/60 | 90/Comp. | 5/10 | — |
| 16 | 168 | 1340 | 0.44 | 140 | 280 | 1/60 | 100/Comp. | 5/10 | — |
| 17 | 24 | 1340 | 0.43 | 160 | 660 | 1/60 | 40/Comp. | 5/10 | — |
| 18 | 20 | 1340 | 0.61 | 200 | 710 | 1/60 | 100/Comp. | 10/20 | — |
| 19 | 24 | 790 | 0.36 | 100 | 110 | 1/60 | 100/Comp. | 30/65 | — |
| 20 | 216 | 790 | 0.86 | 220 | 570 | 1/60 | 150/Comp. | 30/50 | — |
| 22 | 24 | 1320 | 0.38 | 100 | 160 | 1/60 | 90/Comp. | 5/10 | — |
| 23 | 72 | 1320 | 0.79 | 400 | 930 | 1/60 | 130/Consid. | 5/15 | — |
| 24 | 24 | 1320 | 0.30 | 200 | 70 | 1/60 | 100/Comp. | 5/10 | — |
| 25 | 168 | 1320 | 0.70 | 720 | 830 | 1/60 | 200/Consid. | 10/15 | — |
| 28 | 1 | 1320 | 0.42 | 140 | 795 | 1/60 | Consid./Dissol. | 10/10 | — |
| 29 | 24 | 1320 | 0.78 | 500 | 820 | 1/60 | Dissol. | 10/20 | — |
| 30 | 1 | 1320 | 0.45 | 220 | 560 | 1/60 | Dissol. | 10/10 | — |
| 31 | 24 | 1320 | 0.80 | 640 | 880 | 1/60 | Dissol. | 10/10 | — |

As Table IV clearly shows, all of the film samples cast had substantial dry strength properties. In accordance with the teachings of this invention, it should be noted that the wet properties varied greatly as the ionic strength of the liquid media increased. Specifically, in every case, the films were considerably weaker in a distilled water solution as compared with a saline solution. As menstrual fluid is likewise comparable in ionic strength to the saline test solution, the data (see samples 3 and 5) shows that this differential wet property of the films carries through for menstrual fluid as well, making these resins particularly well suited for feminine hygiene products where it is desirable that the resin exhibit greater strength in menstrual fluid then in relatively non-ionic water media such as, for example, tap water. In this connection, it should be noted that several film samples were tested by immersion into tap water, in addition to the usual distilled water vs. 1% sodium chloride solution comparison, in order to evaluate the effect of the salt content in the municipal water supply. The results obtained with tap water were essentially comparable to those obtained with distilled water.

EXAMPLE 5

A series of films are tested for their ability to act as a barrier to fluids while under stress. Film samples, identified by sample number (see Tables 1 and 2), are subjected to hydrostatic pressure from a 2 inch diameter column of fluid. The film to be tested is clamped between rubber gaskets at the bottom of a 2-inch diameter plexiglass column. Fluid is then pumped into the column at a predetermined rate and the bottom surface of the test material is observed through a mirror. The height of fluid head at failure is noted, i.e., the height when a drop of fluid first penetrates through the barrier film. Each of the samples used is a film square about 3 inches by 3 inches and about 2 mil thick. The rate of liquid flow, a 1% saline water solution, is 725 cc/min and the temperature during testing is 25 ± 2° C. Test results are reported in Table V as fluid head at failure per mil of film thickness.

TABLE V

| Sample | Equivalent Weight | Head at Failure Per mil Film Thickness (in/mil) |
|---|---|---|
| 1 | 920 | 3.3 |
| 2 | 970 | 4.5 |
| 3 | 780 | 2.5 |
| 6 | 1392 | 2.4 |

EXAMPLE 6

Films made from Sample 31 (see Table III) are employed in a commercial sanitary napkin in place of the usual polyethylene barrier film. The commercial napkin is a MODESS* feminine napkin sold by the Personal Products Company of Milltown, New Jersey and has the general configuration illustrated in FIGS. 1 and 2 of the drawings. A series of such napkins are tested on a Dynamic Form Testing apparatus, the test comprising suspending the napkin to be tested across a rubber mold which simulates the female form. The form is set into motion by means of a set of gears, cams and rods and simulated menstrual fluid is allowed to drip onto the napkin to closely approximate in-use conditions. The test fluid, comprising 1% sodium chloride, is applied at a rate of about 0.2 cc/min. and the form is operated at a speed of 60 cycles/min. The fluid capacity of the napkin under dynamic conditions is measured by the total volume of fluid applied at the time of failure, i.e., the time at which spotting is noted on the underside of the napkin. Additionally, the condition of the napkin with respect to wear is given a qualitative rating. These results are reported in Table VI along with data corresponding to that of the commercial napkins.

TABLE VI

| Sample | Capacity (cc) | Wear Rating |
|---|---|---|
| 1 | 23 | Excellent |
| 2 | 17 | Very Good |
| 3 | 16.5 | Very Good |
| 4 | 23.0 | Excellent |
| 5 | 21.5 | Excellent |
| 6 | 19.5 | Very Good |
| Commercial Napkin | 16.8–23.0 | Very Good/Excellent |

As the foregoing Tables V and VI illustrate, the barrier films of this invention are comparable to the films now being used in commercial napkins with respect to these abilities to act as a barrier. This notwithstanding, as has been described above, unlike the polyethylene films of commercial napkins, the films of this invention are capable of dispersing in tap water and hence, may be disposed of easily in a water closet.

What is claimed is:

1. In a product for absorbing body fluids including a barrier film for retaining said body fluids, the improvement which comprises employing as said barrier film a polymeric film of a cationic polyurethane having a repeating unit of the formula:

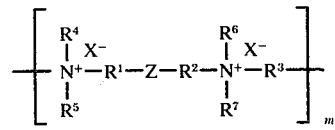

wherein $R^1$ and $R^2$ are selected from the group consisting of $-CH_2-$ and alkylene containing 2 to 4 carbon atoms, inclusive; Z is a linking condensation residue of a polyisocyanate with a polyol and contains at least four urethane linkages; $R^3$ is alkylene containing 2 to 4 carbon atoms, inclusive; $R^4$, $R^5$, $R^6$, and $R^7$ are lower alkyl containing 1 to 4 carbon atoms, inclusive; X is a halogen selected from the group consisting of chlorine and bromine, and m is an integer of sufficient magnitude to form a film; the equivalent weight of the polymer, expressed as the ratio of the molecular weight of the repeating unit divided by the number of $R^+$ in the repeating unit, being from about 500 to about 2000, whereby said film is resistant to body fluids but dispersible in water.

2. The product in accordance with claim 1 wherein the equivalent weight of the polymer is about 750 to about 1400.

3. The product in accordance with claim 1 wherein the cationic polyurethane includes a condensation product of a polyisocyanate and an aliphatic polyester polyol.

4. The product in accordance with claim 1 wherein the molecular weight of said cationic polyurethane is in the range of about 8000 to about 50,000.

5. The product in accordance with claim 1 wherein $R^1$ and $R^2$ are both ethylene, $R^3$ is butenylene, $R^4$, $R^5$, $R^6$ and $R^7$ methyl, and X is chlorine.

6. The product in accordance with claim 1 wherein Z contains, in addition to said urethane linkages, also ester linkages and ether linkages.

7. The product in accordance with claim 1 wherein Z contains, in addition to said urethane linkages, also ester linkages.

8. The product in accordance with claim 1 wherein Z contains, in addition to said urethane linkages, also ether linkages.

9. The product in accordance with claim 1 which is a disposable diaper wherein said body fluid containing means is an absorbent pad having a backing sheet made from said barrier film.

10. The product in accordance with claim 1 which is a sanitary napkin wherein said body fluid containing means is an absorbent core and wherein said barrier film overlies the bottom surface of the absorbent core.

11. The product in accordance with claim 10 wherein the barrier film is disposed between a pair of absorbent layers in said absorbent core.

* * * * *

UNITED STATES PATENT OFFICE
CERTIFICATE OF CORRECTION

Patent No. 4,011,871  Dated March 15, 1977

Inventor(s) Arnold Jay Taft

It is certified that error appears in the above-identified patent and that said Letters Patent are hereby corrected as shown below:

In column 1, line 64, "Preferably molecular weight" should read -- Preferably the molecular weight --.

In Column 7, line 9, "according" should read --- accruing ---.

In Column 11, Table IV, the second column, Cure Time (HRS.), line 15, "20" should read --- 120 ---.

In Column 14, Claim 1, lines 40-41, "of sufficient magnitude to form a film;" should read --- of sufficient magnitude to provide a polymer of sufficient magnitude to form a film; ---.

In Column 14, line 43, "R+ " should read --- N+ ---.

Signed and Sealed this

Eleventh Day of October 1977

[SEAL]

Attest:

RUTH C. MASON
Attesting Officer

LUTRELLE F. PARKER
Acting Commissioner of Patents and Trademarks